US011585736B2

(12) United States Patent
Wang et al.

(10) Patent No.: US 11,585,736 B2
(45) Date of Patent: Feb. 21, 2023

(54) HYDROCARBON GENERATION PYROLYSIS SIMULATION EXPERIMENTAL DEVICE FOR CENTRIFUGAL CONTINUOUS GAS SAMPLING OF HYDROCARBON SOURCE ROCK

(71) Applicant: GUANGZHOU INSTITUTE OF GEOCHEMISTRY, CHINESE ACADEMY OF SCIENCES, Guangdong (CN)

(72) Inventors: Qiang Wang, Guangdong (CN); Jinzhong Liu, Guangdong (CN); Ping-An Peng, Guangdong (CN)

(73) Assignee: GUANGZHOU INSTITUTE OF GEOCHEMISTRY, CHINESE ACADEMY OF SCIENCES, Guangdong (CN)

( * ) Notice: Subject to any disclaimer, the term of this patent is extended or adjusted under 35 U.S.C. 154(b) by 0 days.

(21) Appl. No.: 17/423,851

(22) PCT Filed: Jul. 9, 2020

(86) PCT No.: PCT/CN2020/101005
§ 371 (c)(1),
(2) Date: Jul. 16, 2021

(87) PCT Pub. No.: WO2021/051968
PCT Pub. Date: Mar. 25, 2021

(65) Prior Publication Data
US 2022/0205880 A1 Jun. 30, 2022

(30) Foreign Application Priority Data
Sep. 18, 2019 (CN) .................. 201910880832.X

(51) Int. Cl.
*G01N 1/22* (2006.01)
*G01N 1/24* (2006.01)
(Continued)

(52) U.S. Cl.
CPC .............. *G01N 1/2226* (2013.01); *G01N 1/24* (2013.01); *G01N 25/00* (2013.01); *G01N 30/14* (2013.01); *G01N 2030/125* (2013.01)

(58) Field of Classification Search
CPC ........ G01N 1/2226; G01N 1/24; G01N 25/00; G01N 30/02; G01N 2030/125;
(Continued)

(56) References Cited

U.S. PATENT DOCUMENTS

| 4,578,356 | A | | 3/1986 | Larter | |
|---|---|---|---|---|---|
| 5,201,219 | A | * | 4/1993 | Bandurski | ............. E21B 49/005 73/19.01 |
| 2016/0341707 | A1 | | 11/2016 | Inan | |

FOREIGN PATENT DOCUMENTS

| CN | 201291132 Y | 8/2009 |
|---|---|---|
| CN | 103149291 A | 6/2013 |

(Continued)

*Primary Examiner* — Nimeshkumar D Patel
*Assistant Examiner* — Nashmiya S Fayyaz
(74) *Attorney, Agent, or Firm* — Global IP Services; Tianhua Gu

(57) ABSTRACT

A hydrocarbon generation pyrolysis simulation experimental device for centrifugal continuous gas sampling of a hydrocarbon source rock, including a centrifugal turntable, a motor, a quartz sample tube, a heating set, a cooling set, a rotary joint mounted coaxially with a rotating shaft of the centrifugal turntable, a vacuum pump, and vacuum gas collecting pipes, wherein a sealing plug is arranged at an orifice of the quartz sample tube, a thermocouple and a first exhaust pipeline connected with an inlet of the rotary joint are mounted on the sealing plug, the rotary joint is communicated with a vacuum pump through a second exhaust
(Continued)

pipeline, a plurality of vacuum gas collecting pipes are respectively communicated with the second exhaust pipeline through an electromagnetic valve, a vacuum pump switching valve is mounted on the second exhaust pipeline at an inlet end of the vacuum pump, and a control circuit board is mounted on the centrifugal turntable.

6 Claims, 3 Drawing Sheets

(51) Int. Cl.
*G01N 25/00* (2006.01)
*G01N 30/14* (2006.01)
*G01N 30/12* (2006.01)

(58) Field of Classification Search
CPC .......... G01N 33/241; G01N 9/30; G01N 1/02; G01N 1/22
USPC ...................................................... 73/863.12
See application file for complete search history.

(56) References Cited

FOREIGN PATENT DOCUMENTS

| CN | 103270240 A | * | 8/2013 | ............. E21B 43/20 |
|---|---|---|---|---|
| CN | 103323366 A | | 9/2013 | |
| CN | 105765380 A | * | 7/2016 | ............. G01N 33/24 |
| CN | 110595938 A | | 12/2019 | |
| WO | WO-2019145745 A1 | * | 8/2019 | ........... G01N 33/241 |

* cited by examiner

HYDROCARBON GENERATION PYROLYSIS SIMULATION EXPERIMENTAL DEVICE FOR CENTRIFUGAL CONTINUOUS GAS SAMPLING OF HYDROCARBON SOURCE ROCK

CROSS REFERENCE TO RELATED PATENT APPLICATION

The present application is the US national stage of PCT/CN2020/101005 filed on Jul. 9, 2020, which claims the priority of the Chinese patent applications No. 201910880832.X filed on Sep. 18, 2019, which application is incorporated herein by reference.

TECHNICAL FIELD

The present invention relates to a hydrocarbon generation pyrolysis simulation experimental device for centrifugal continuous gas sampling of a hydrocarbon source rock.

BACKGROUND

A hydrocarbon source rock is pyrolyzed to generate oil and gas through a pyrolysis simulation experiment method, which is one of the important means to evaluate a gas generation volume of the hydrocarbon source rock. In a pyrolysis simulation process, the generated oil needs to be moved out of a heating area in time to avoid secondary pyrolysis of the oil.

In a current experiment of generating natural gas by pyrolysis simulation, a gold tube is mainly used as a reaction vessel, which means that a sample is placed in the gold tube and heated to generate gas. A limited and closed hydrocarbon generation environment of the gold tube is quite different from a natural hydrocarbon generation environment. In a natural stratum, oil generated by a geothermal action may leave the heating area through a migration action of a rock fracture, thus avoiding or weakening a gas generation effect of pyrolysis of the oil. However, since the gold tube is a closed and limited system, the oil generated by pyrolysis simulation cannot be discharged in time. The oil is pyrolyzed to generate gas at a high temperature, so that a gas generation volume is significantly higher than that in the stratum. Another pyrolysis simulation experiment method is that the generated oil is blown out by using flowing carrier gas, but this method is not effective in practice, because an excessively high flow rate of the carrier gas will dilute the natural gas, which leads to a difficulty in next analysis. If the flow rate of the carrier gas is excessively low, the oil cannot be effectively blown out of the heating area. In addition to the above reason, in a pyrolysis simulation gas generation experiment, it is necessary to collect gas generated by the hydrocarbon source rock at different temperature stages, thus providing data for hydrocarbon generation kinetics. Up to now, there are no experimental instruments in the market that can meet the above requirements.

SUMMARY

The present invention aims to overcome the defects in the prior art above, and provides a hydrocarbon generation pyrolysis simulation experimental device for centrifugal continuous gas sampling of hydrocarbon source rock with a high experimental efficiency and a low analysis error.

In order to achieve the above objective, the technical solutions used in the present invention are as follows: a hydrocarbon generation pyrolysis simulation experimental device for centrifugal continuous gas sampling of a hydrocarbon source rock includes a centrifugal turntable, a motor for driving the centrifugal turntable to rotate, a quartz sample tube mounted on the centrifugal turntable, a heating set sleeved on an upper part of the quartz sample tube, a cooling set arranged on a lower part of the quartz sample tube, a rotary joint mounted coaxially with a rotating shaft of the centrifugal turntable, a vacuum pump, and a plurality of vacuum gas collecting pipes, wherein a sample placing flange is arranged at a middle inner wall of the quartz sample tube, a sealing plug is arranged at an orifice of the quartz sample tube, a thermocouple and a first exhaust pipeline are mounted on the sealing plug, an outlet of the rotary joint is communicated with an inlet of a vacuum pump through a second exhaust pipeline, the plurality of vacuum gas collecting pipes are respectively communicated with the second exhaust pipeline through an electromagnetic valve, a vacuum pump switching valve is mounted on the second exhaust pipeline at an inlet end of the vacuum pump, a control circuit board is also mounted on the centrifugal turntable, and the thermocouple, the heating set, and the cooling set are respectively connected with the control circuit board.

Further, the heating set includes a copper alloy block fixed on the centrifugal turntable, a heating hole of the quartz sample tube is formed in the copper alloy block, two sides of the heating hole are respectively provided with a heating rod, and a thermal insulation asbestos board is mounted on one side face of the copper alloy block.

The cooling set includes a red copper block fixed on the centrifugal turntable, two sides of the red copper block are respectively provided with a heat insulation foam board and a semiconductor refrigerating assembly, and a cooling hole for accommodating a lower part of the quartz sample tube is formed in the red copper block.

Further, an electric brush is also mounted on an output shaft of the motor for supplying power to the control circuit board, the heating set, and the cooling set.

Further, a vacuum sensor is also arranged on the vacuum pump.

Further, a counterweight block is also mounted on the centrifugal turntable, and the counterweight block is located at a symmetrical position of the quartz sample tube.

The present invention has the beneficial effects that by adopting the above structure, the present invention has the advantages of a high experimental efficiency and a low analysis error. Oil generated by pyrolysis simulation can be effectively transferred to a low-temperature area in the lower part of the quartz sample tube, thus avoiding secondary pyrolysis of the oil; and gas generated at different temperatures is collected in sections for analysis. According to experimental results, an oil and gas generation process under an open system of a stratum may be simulated, and meanwhile, a maximum oil generation volume, a maximum natural gas generation volume, and hydrocarbon generation kinetic parameters are obtained.

BRIEF DESCRIPTION OF THE DRAWINGS

The present invention is further described in detail hereinafter with reference to the accompanying drawings.

DETAILED DESCRIPTION

Figure 1:
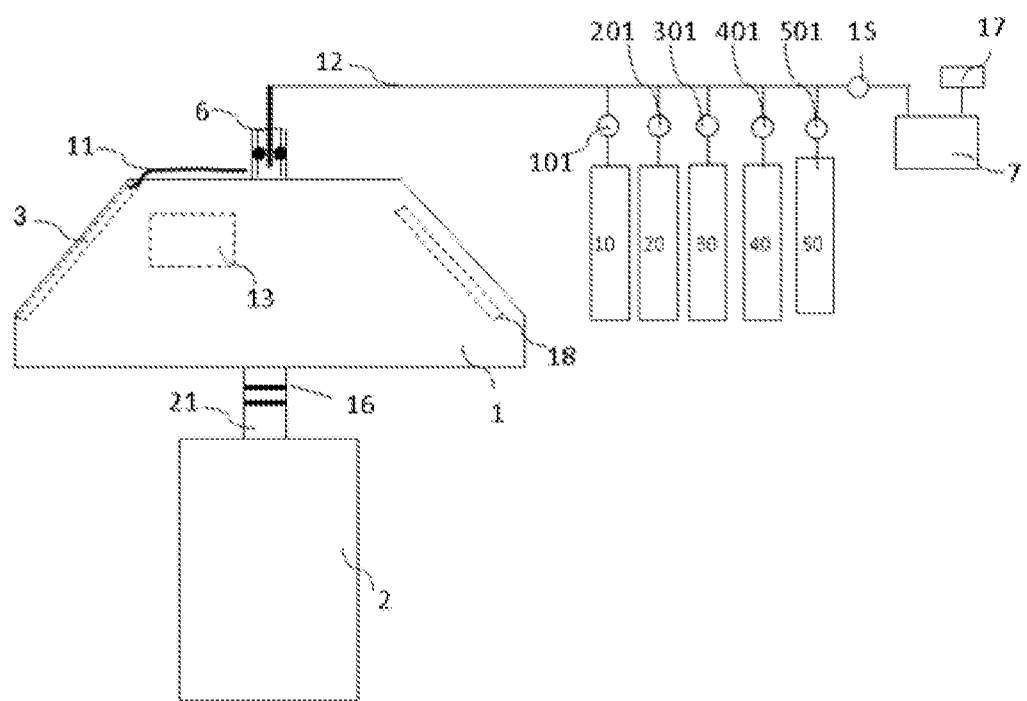
FIG. 1 is a schematic diagram of a structure of the present invention.
Figure 2:
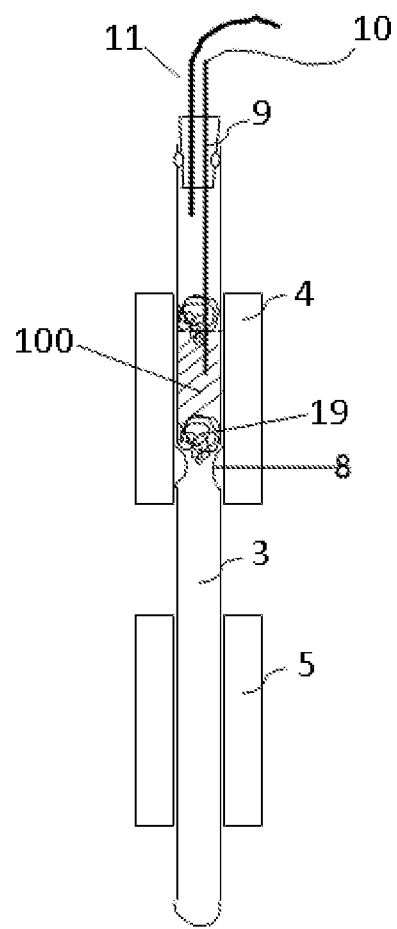
FIG. 2 is a schematic diagram of a structure of a quartz sample tube part in the present invention.

As shown in FIG. 1 and FIG. 2, a hydrocarbon generation pyrolysis simulation experimental device for centrifugal continuous gas sampling of a hydrocarbon source rock according to the present invention includes a centrifugal turntable 1, a motor 2 for driving the centrifugal turntable to rotate, a quartz sample tube 3 mounted on the centrifugal turntable, a heating set 4 sleeved on an upper part of the quartz sample tube, a cooling set 5 arranged on a lower part of the quartz sample tube, a rotary joint 6 mounted coaxially with a rotating shaft of the centrifugal turntable, a vacuum pump 7, and a plurality of vacuum gas collecting pipes.

As shown in FIG. 2, a sample placing flange 8 is arranged at a middle inner wall of the quartz sample tube 3, a sealing plug 9 is arranged at an orifice of the quartz sample tube, and a thermocouple 10 and a first exhaust pipeline 11 are mounted on the sealing plug 9. One end of the first exhaust pipeline 11 is communicated with an inner cavity of the quartz sample tube 3, and the other end of the first exhaust pipeline is connected with an inlet of the rotary joint 6. An outlet of the rotary joint 6 is communicated with an inlet of the vacuum pump 7 through a second exhaust pipeline 12. A control circuit board 13 is also mounted on the centrifugal turntable 1, and the thermocouple 10, the heating set 4, and the cooling set 5 are respectively connected with the control circuit board 13. An electric brush 16 is also mounted on an output shaft of the motor 2 for supplying power to the control circuit board 13, the heating set 4, and the cooling set 5.

In the embodiment, five vacuum gas collecting pipes are provided, and each vacuum gas collecting pipe is respectively communicated with the second exhaust pipeline 12 through an electromagnetic valve. Specifically, the five vacuum gas collecting pipes are respectively a first vacuum gas collecting pipe 10, a second vacuum gas collecting pipe 20, a third vacuum gas collecting pipe 30, a fourth vacuum gas collecting pipe 40, and a fifth vacuum gas collecting pipe 50. Corresponding electromagnetic valves are sequentially a first electromagnetic valve 101, a second electromagnetic valve 102, a third electromagnetic valve 103, a fourth electromagnetic valve 104, and a fifth electromagnetic valve 105.

A vacuum pump switching valve 15 is mounted on the second exhaust pipeline 12 at an inlet end of the vacuum pump 7.

Figure 3:
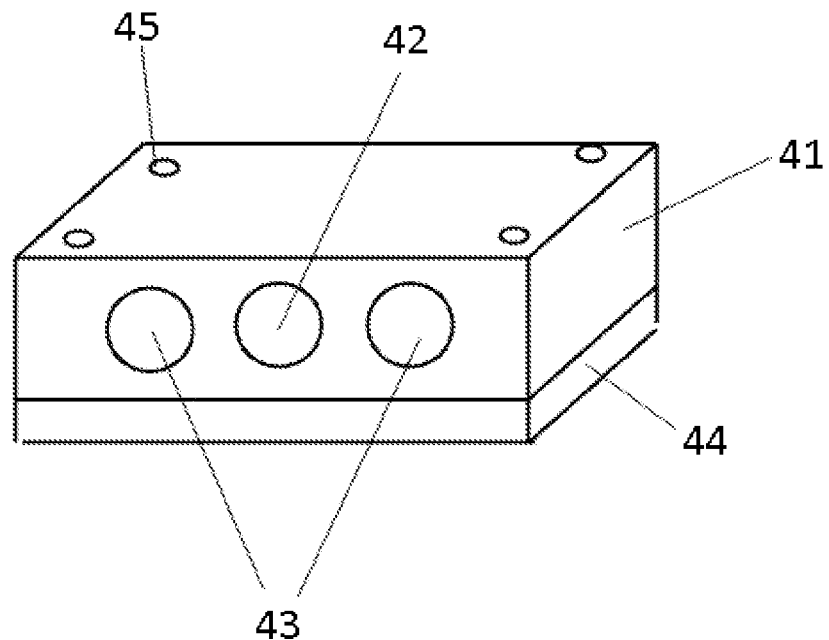
FIG. 3 is a schematic diagram of a structure of a heating set in the present invention.

Further, as shown in FIG. 3, the heating set includes a copper alloy block 41, a heating hole 42 of the quartz sample tube is formed in the copper alloy block, two sides of the heating hole are respectively provided with a heating rod 43, and a thermal insulation asbestos board 44 is mounted on one side face of the copper alloy block. A screw mounting hole 45 is also formed in the copper alloy block 41, and the copper alloy block 41 is fixedly connected with the centrifugal turntable 1 through a screw.

Figure 4:
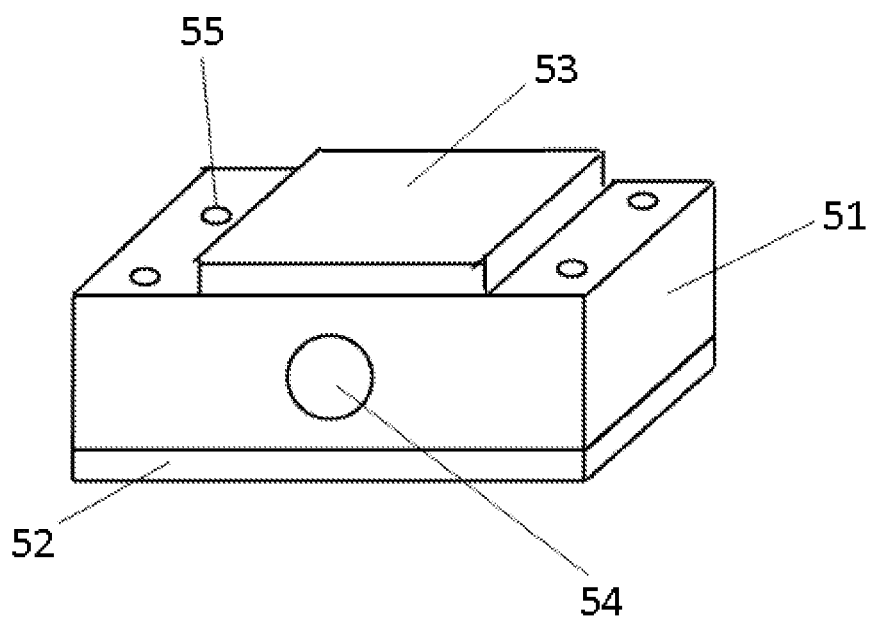
FIG. 4 is a schematic diagram of a structure of a cooling set in the present invention.

As shown in FIG. 4. the cooling set 5 includes a red copper block 51 fixed on the centrifugal turntable, two sides of the red copper block 51 are respectively provided with a heat insulation foam board 52 and a semiconductor refrigerating assembly 53, and a cooling hole 54 for accommodating a lower part of the quartz sample tube is formed in the red copper block 51. A screw hole 55 is also formed in the red copper block 51, and the copper alloy block 41 is fixedly connected with the centrifugal turntable 1 through a screw.

Further, a vacuum sensor 17 is also arranged on the vacuum pump 7. In addition, a counterweight block 18 is also mounted on the centrifugal turntable 1, and the counterweight block 18 is located at a symmetrical position of the quartz sample tube 3. By arranging the counterweight block 18, the centrifugal turntable 1 can rotate more smoothly.

Specific operating steps of performing the pyrolysis simulation experiment by using the present invention are as follows.

(1) According to FIG. 2, a hydrocarbon source rock sample 100 is placed on a quartz wool 19 and then placed on the sample placing flange 8 of the quartz sample tube, and an upper part of the sample is also covered with a quartz wool.

(2) The first exhaust pipeline 11 and the thermocouple are respectively connected with the sealing plug 9 on the quartz sample tube, and the quartz sample tube is fixedly mounted on the centrifugal turntable 1.

(3) All electromagnetic valves and all vacuum pump switching valves 15 are opened, and the vacuum pump 7 is opened to vacuumize the whole system for 10 minutes.

(4) All electromagnetic valves and all vacuum pump switching valves 15 are closed.

(5) The first electromagnetic valve 101 is opened, the motor 2 is started, the heating set 4 is started to heat after reaching a rated rotating speed, a heating rate is set to be 120° C./h, a first temperature point is set to be 300° C., and in a heating process, the gas generated by the sample is collected into the first gas collecting pipe 10.

(6) The first electromagnetic valve 101 is closed, the first electromagnetic valve 102 is opened, the quartz sample tube is continuously heated to 350° C., and in the heating process, the gas generated by the sample is collected into the second gas collecting pipe 20.

(7) By analogy, the heating is performed to 500° C.

(8) The fifth electromagnetic valve 105 is closed, the heating is stopped, and the motor 2 is stopped rotating.

(9) After the centrifugal turntable 1 is completely stopped, the second exhaust pipeline 12 is removed from the rotary joint 6 and connected with a sample inlet of a gas chromatograph, and gas yield analysis and isotope analysis are performed on gases in the five gas collecting pipes 10, 20, 30, 40 and 50 in sequence.

(10) After the quartz sample tube 3 is completely cooled, the quartz sample tube is removed, the sealing plug 9 at a top part is removed, the quartz wool at the top part of the sample is taken out with a steel wire hook, dichloromethane is injected into the quartz sample tube, the sealing plug 9 at the top part of the quartz sample tube is tightened with a polytetrafluoroethylene plug, and the mixture is placed in an ultrasonic oscillator to extract oil from the rock sample.

(11) Conventional operations such as filtration and volume metering are performed on a solution containing the oil, and then gas chromatographic analysis is performed.

(12) After the solvent is volatilized, a yield of heavy hydrocarbon (nonvolatile oil) is determined by weighing.

(13) The heating rate is set to be 12° C./h, and steps 1 to 12 are repeated.

(14) So far, gas yield curves of two heating rates are obtained. According to gas yields at different temperatures, hydrocarbon generation kinetic parameters of single components (methane, ethane, propane) of the gas are calculated by Kinetic software.

The above contents are only used to illustrate the technical solutions of the present invention, and simple modifications or equivalent substitutions made by those of ordinary skills in the art do not depart from the essence and scope of the technical solutions of the present invention.

What is claimed is:

1. A hydrocarbon generation pyrolysis simulation experimental device for centrifugal continuous gas sampling of a hydrocarbon source rock, comprising
a centrifugal turntable, a motor for driving the centrifugal turntable to rotate, a quartz sample tube for containing hydrocarbon source rock sample mounted on the centrifugal turntable, a heating set sleeved on an upper part of the quartz sample tube, a cooling set arranged on a lower part of the quartz sample tube, a rotary joint mounted coaxially with a rotating shaft of the centrifugal turntable, a vacuum pump, and a plurality of vacuum gas collecting pipes, wherein
a sample placing flange is arranged at a middle inner wall of the quartz sample tube, a sealing plug is arranged at an orifice of the quartz sample tube, a thermocouple and a first exhaust pipe are mounted on the sealing plug, an outlet of the rotary joint is communicated with an inlet of the vacuum pump through a second exhaust pipe, each one of the plurality of vacuum gas collecting pipes is communicated with the second exhaust pipe through an electromagnetic valve, a vacuum pump switching valve is mounted on the second exhaust pipe at an inlet end of the vacuum pump, a control circuit board is also mounted on the centrifugal turntable, and the thermocouple, the heating set, and the cooling set are respectively connected with the control circuit board.

2. The hydrocarbon generation pyrolysis simulation experimental device for the centrifugal continuous gas sampling of the hydrocarbon source rock according to claim 1, wherein the heating set comprises a copper alloy block fixed on the centrifugal turntable, a heating hole of the quartz sample tube is formed in the copper alloy block, two sides of the heating hole are respectively provided with a heating rod, and a thermal insulation asbestos board is mounted on one side face of the copper alloy block.

3. The hydrocarbon generation pyrolysis simulation experimental device for the centrifugal continuous gas sampling of the hydrocarbon source rock according to claim 1, wherein the cooling set comprises a red copper block fixed on the centrifugal turntable, two sides of the red copper block are respectively provided with a heat insulation foam board and a semiconductor refrigerating assembly, and a cooling hole for accommodating the lower part of the quartz sample tube is formed in the red copper block.

4. The hydrocarbon generation pyrolysis simulation experimental device for the centrifugal continuous gas sampling of the hydrocarbon source rock according to claim 1, wherein an electric brush is also mounted on an output shaft of the motor for supplying power to the control circuit board, the heating set, and the cooling set.

5. The hydrocarbon generation pyrolysis simulation experimental device for the centrifugal continuous gas sampling of the hydrocarbon source rock according to claim 1, wherein a vacuum sensor is also arranged on the vacuum pump.

6. The hydrocarbon generation pyrolysis simulation experimental device for the centrifugal continuous gas sampling of the hydrocarbon source rock according to claim 1, wherein a counterweight block is also mounted on the centrifugal turntable, and the counterweight block is located at a symmetrical position of the quartz sample tube.

* * * * *